(12) United States Patent
Adams et al.

(10) Patent No.: US 11,821,041 B2
(45) Date of Patent: Nov. 21, 2023

(54) NON-INVASIVE TEST TO PREDICT RECURRENCE OF COLORECTAL CANCER

(71) Applicant: Roche Sequencing Solutions, Inc., Pleasanton, CA (US)

(72) Inventors: Hans-Peter Adams, Postsdam (DE); Aarthi Balasubramanyam, Sunnyvale, CA (US); Bernd Hinzmann, Berlin (DE); John Lee, Walnut Creek, CA (US); John Palma, Alamo, CA (US); Andre Rosenthal, Ludwigsfelde (DE); Urich-Peter Rohr, Lorrach (DE)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 442 days.

(21) Appl. No.: 16/534,028

(22) Filed: Aug. 7, 2019

(65) Prior Publication Data

US 2019/0360059 A1    Nov. 28, 2019

Related U.S. Application Data

(63) Continuation of application No. PCT/EP2018/052750, filed on Feb. 5, 2018.

(60) Provisional application No. 62/455,760, filed on Feb. 7, 2017.

(51) Int. Cl.
| | |
|---|---|
| *C12Q 1/68* | (2018.01) |
| *C12Q 1/6886* | (2018.01) |
| *G16B 20/20* | (2019.01) |

(52) U.S. Cl.
CPC ........... *C12Q 1/6886* (2013.01); *G16B 20/20* (2019.02); *C12Q 2600/106* (2013.01); *C12Q 2600/112* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

2016/0032396 A1    2/2016    Diehn et al.

OTHER PUBLICATIONS

Ryan et al; Gut, 2003, vol. 52, pp. 101-108.*
Niu et al; Biomed Research International; vol. 2014, pp. 1-7, article ID 214727.*
Ashford, M., Roche Previews RUO CAPP-Seq Liquid Biopsy Assays at AMP Meeting, Shares Early User Data, 360 Dx, Nov. 11, 2016, retrieved from the Internet, Roche.
Bratman, S. V. et al, Potential clinical utility of ultrasensitive circulating tumor DNA detection with CAPP-Seq, Expert Rev Mol Diagn, (2015), pp. 715-719, vol. 15 No. 6.
International Search Report and Written Opinion, PCTEP2018052750, dated Apr. 23, 2018.
Lanman, R. B. et al, Analytical and Clinical Validation of a Digital Sequencing Panel for Quantitative, Highly Accurate Evaluation of Cell-Free Circulating Tumor DNA, PLOS One, (2015), pp. e0140712, vol. 10, No. 10.
Newman, A. M. et al, Integrated digital error suppression for improved detection of circulating tumor DNA, Nature Biotechnology, (2016), pp. 547-555, vol. 34, No. 5.
Reinert, T. et al, Analysis of circulating tumour DNA to monitor disease burden following colorectal cancer surgery, Gut, (2016), pp. 625-634, vol. 65, No. 4.
Roche, Avenio ctDNA Surveillance Kit coverage for lung and CRC serial tumor burden monitoring, Tumor Burden Monitoring, Jul. 31, 2017, retrieved from the Internet.
Tadayuki Kou, et al, The possibility of clinical sequencing in the management of cancer, Jpn J Clin Oncol, (2016), pp. 399-406, vol. 46, No. 5.
Tie J. et al, Circulating tumor DNA analysis detects minimal residual disease and predicts recurrence in patients with stage II colon cancer, Science Translational Medicine, (2016), pp. 346ra92-346ra92, vol. 8, No. 346.

* cited by examiner

*Primary Examiner* — Jehanne S Sitton
(74) *Attorney, Agent, or Firm* — Eric Grant Lee

(57) ABSTRACT

The invention is a method of predicting recurrence of colorectal cancer in a patient following surgery, the method comprising analysis of circulating tumor DNA from a patient's sample.

4 Claims, 5 Drawing Sheets

NON-INVASIVE TEST TO PREDICT RECURRENCE OF COLORECTAL CANCER

CROSS-REFERENCE TO RELATED APPLICATIONS

This application is a continuation of the International Application Ser. No. PCT/EP2018/052750 filed on Feb. 5, 2018, which claims priority to the U.S. Provisional Application Ser. No. 62/455,760 filed on Feb. 7, 2017. Each of the above patent applications is incorporated herein by reference as if set forth in its entirety.

FIELD OF THE INVENTION

The invention relates to the field of oncology. More specifically, the invention relates to the field of nucleic acid-based testing of cancer patients.

BACKGROUND OF THE INVENTION

Patients with colorectal cancer (CRC) will routinely have surgery with the intent to cure. Adjuvant chemotherapy is offered following surgery but risk stratification strategies for these patients remain suboptimal. There is a need for a reliable predictor of tumor recurrence for guiding patient therapy.

SUMMARY OF THE INVENTION

In some embodiments, the invention is a method for identifying a colorectal cancer patient as likely to experience recurrence of the cancer following surgery comprising the steps of: providing a cell-free blood sample obtained from the patient following surgery; determining the sequence of at least a portion of each of the genes listed in Table 1; identifying the patient as likely to experience recurrence of the cancer if at least one mutation is found in the sequence or identifying the patient as not likely to experience recurrence of the cancer if no mutations are found in the sequence determined in step. In some embodiments, the patient is a stage II or stage III colorectal cancer patient. In some embodiments, the patient has clear histological margins of the tumor at the time of surgery. In some embodiments, the method further comprises a step of administering adjuvant therapy if the patient is identified as likely to experience recurrence of the cancer. In some embodiments, the method further comprises a step of modifying a chemotherapy regimen, e.g., reducing or increasing the dose of oxaliplatin. In some embodiments, the adjuvant therapy is selected from immune modulating agents, molecular targeted agents or additional chemotherapeutic agents.

In some embodiments, the invention is a method of treatment of a colorectal cancer patient comprising the steps of: providing a cell-free blood sample obtained from the patient following surgery; determining the sequence of at least a portion of each of the genes listed in Table 1; identifying the patient as likely to experience recurrence of the cancer if at least one mutation is found in the sequence; or identifying the patient as not likely to experience recurrence of the cancer if no mutations are found in the sequence; administering adjuvant chemotherapy if the patient identified as likely to experience recurrence of the cancer. In some embodiments, the patient undergoing treatment is stage II or III colorectal cancer patient. In some embodiments, the adjuvant therapy included in the treatment is selected from immune modulating agents, molecular targeted agents or additional chemotherapeutic agents.

In some embodiments, the invention is a computer system designed to implement an algorithm for detecting mutations in a sample from colorectal cancer patient, wherein the algorithm analyses sequencing data on biomarkers from Table 1 and contains one or more steps selected from mutation detection, mutation frequency scoring, controlling for germ-line variation, error correction and final determination whether the sample is mutation-positive.

DETAILED DESCRIPTION OF THE INVENTION

Definitions

Figure 1:
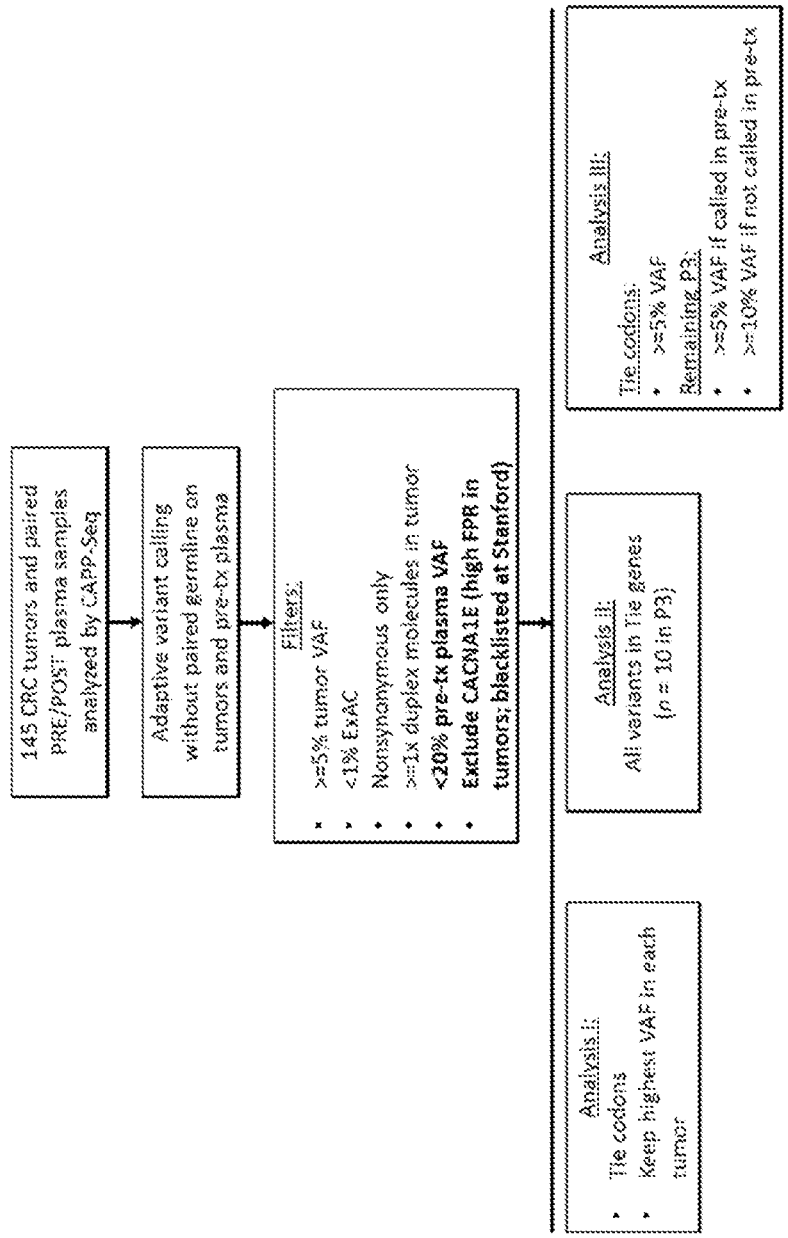
FIG. 1 illustrates an analysis flow chart for mutation calls of CRC patients.

The following definitions are not limiting but merely aid in understanding this disclosure.

The term "RFS" is used herein to describe the time of Recurrence Free Survival for a patient.

The term "TTR" is used herein to describe the Total Time to Recurrence for a patient.

The term "OS" is used herein to describe the time of Overall Survival for a patient.

The term "CAPP-Seq" is used herein to describe a method of analyzing cell-free tumor DNA in a patient disclosed in U.S. patent application Ser. Nos. 14/209,807, 14/774,518 and International Application Ser. No. PCT/US2015/049838 titled "Identification and Use of Circulating Tumor Markers."

The term "R0 patient" is used herein to describe a patient having clear histological margins from resected tissue.

The term "R1 patient" is used herein to describe a patient having microscopic residual disease in surgically resected tissue.

The term "circulating tumor DNA (ctDNA)" is used herein to describe a portion of cell-free DNA found in human blood plasma or serum that originates from the tumor. Circulating tumor DNA is distinguished from non-tumor DNA by the mutations characteristic of the tumor. In the context of the present invention, detecting ctDNA means detecting mutated cell-free DNA.

The term "biomarker" is used herein to describe a nucleotide sequence that contains information relevant to the biological or clinical phenomenon. For example, the information may be a mutation status of the sequence. The biomarker can be a gene (including coding sequence, regulatory sequence, intron or a splice site) or an intergenic region. The clinical phenomenon can be the presence of malignant cells, e.g., tumor cells in a patient's sample.

Patients with colorectal cancer in stage II and III will routinely have surgery with the intent to cure. The use of adjuvant chemotherapy is tumor stage dependent: The US National Comprehensive Cancer Network (NCCN) guidelines suggest multiple treatment options for stage II colon cancer patients, ranging from observation to a variety of chemotherapy modalities. These options are based on the observation derived from meta-analyses and large randomized trials, e.g. the QUASAR Study, that there is no—or only marginal—gain with fluoropyrimidine-based adjuvant chemotherapy if all patients with colon cancer are treated at stage II. Thus, it cannot be generally recommended as a standard of care. Approximately 15-20% of stage II patients experience a relapse after curative surgery. Therefore, there is an unmet need for molecular markers that can distinguish patients with stage II colon cancer who are high-risk for relapse.

A diagnosis of stage III CRC indicates the presence of lymph node metastases where NCCN guidelines recommend systemic chemotherapy after surgery in order to increase the chance of a cure. The choices of chemotherapy range from 5FU based regimens to the addition of oxaliplatin to 5FU-based regimens; at least 5 different regimens are listed as per guidelines. It can be assumed that not all patients benefit from adjuvant chemotherapy, in particular the additional contribution of oxaliplatin for curation is around 3-5%. Therefore, there is an unmet need for molecular markers that can distinguish patients with stage III colon cancer who are at lower risk and might benefit from less toxic chemotherapeutic regimens or are identified with high risk that need more toxic but also more potent chemotherapeutic treatment such as FOLFOX or FOLFOXIRI.

Based on the current technologies, it is challenging to predict which patients would benefit the most from adjuvant chemotherapy among the CRC patients. For example, Tie, J., et al. (2016) *Circulating tumor DNA analysis detects minimal residual disease and predicts recurrence in patients with stage II colon cancer*, Sci Trans' Med. 8(346):346ra92.

In some embodiments, the invention utilized a blood sample from a patient. The sample can include any fraction of blood, e.g., serum or plasma, which contains cell-free DNA including circulating tumor DNA (cfDNA or ctDNA). In some embodiments, the sample is taken serially at various times during treatment, e.g., before and after surgery or before, after and during a chemotherapy regimen. In some embodiments, a tumor sample and a corresponding blood sample are taken post-surgery. In some embodiments, the sample is taken 1-21 days post-surgery. The tumor and blood sample can be collected by a suitable means that preserves the DNA therein, including formalin-fixed paraffin embedding (FFPE) tissue, fresh frozen tissue or blood tissue collected in a preservative medium.

In some embodiments, the invention utilizes a biomarker panel, including a gene panel or a mutation panel or a somatic variant panel. The mutations may include single-nucleotide variations (SNVs), deletions and insertions (indels) that correspond to on-sense missense and frame-shift mutations if they occur in the coding regions of genes. Other types of mutations include gene fusions and translocations. The selection, size and content of such panels has been described e.g., in U.S. patent application Ser. Nos. 14/209,807, 14/774,518 and International App. No. PCT/US2015/049838 titled "Identification and Use of Circulating Tumor Markers." In some embodiments, the invention includes determining the sequence of the biomarkers in the panel, e.g., the genes listed in Table 1. In some embodiments, the entire sequence of a gene is determined. In other embodiments, the entire coding sequence of a gene is determined. In other embodiments, only the sequence of a portion of the gene known to undergo mutagenesis in cancer is determined. In yet other embodiments, the biomarker is not associated with a coding sequence but is associated with a regulatory sequence or a sequence of unknown function known to be mutated in human tumors.

In the context of the present invention, the sequence of a biomarker can be determined via any suitable method known in the art. The suitable method would have sufficient accuracy, e.g., sensitivity and specificity to detect rare sequences with a low rate of errors. In some embodiments, the sequencing method includes an error correction step, such as use of molecular barcodes, error stereotyping and other chemical or computation methods of error suppression as described e.g., in see the patent applications "Identification and Use of Circulating Tumor Markers", supra. The sequencing method may include a massively parallel sequencing method, including an array based sequencing (Illumina, San Diego, Cal.), an emulsion-based sequencing (ThermoFisher, Waltham, Mass.) an optical measurement based sequencing (Pacific BioSciences, Menlo Park, Cal.) or a nanopore-based sequencing (Roche Sequencing Solutions, Santa Clara, Cal.).

In some embodiments, the invention utilizes a biomarker panel, such as AVENIO® ctDNA Analysis Kit (Roche Sequencing Solutions, Inc., Pleasanton, Cal.) that is capable of analyzing the blood of patients after surgery to identify whether patients have circulating tumor DNA (ctDNA). The examples describe several embodiments of the invention. (FIG. 1). In some embodiments, a panel that represents NCCN guideline recommended biomarkers for targeted therapies (17 genes) is used. In other embodiments, a broader panel further including therapy resistance markers (total 60 genes) is used. In yet another example, a broader panel further including cancer hotspot mutations (total 180 genes) is used (see the patent applications "Identification and Use of Circulating Tumor Markers", supra). The composition of the biomarker panel in AVENIO® ctDNA Analysis Kit is shown in Table 1.

TABLE 1

| Composition of the biomarker panel | | | | | | | |
|---|---|---|---|---|---|---|---|
| ABCC5 | CSMD1 | FAT1 | HTR1E | MAP7D3 | PIK3CA | SV2A | AR |
| ABCG2 | CSMD3 | FBN2 | HTR2C | MKRN3 | PIK3CG | T | CCND1 |
| ACTN2 | CTNNB1 | FBXL7 | IFI16 | MMP16 | PKHD1L1 | THSD7A | CCND2 |
| ADAMTS12 | CTNND2 | FBXW7 | IL7R | MTX1 | POLE | TIAM1 | CCND3 |
| ADAMTS16 | CYBB | FCRL5 | INSL3 | MYH7 | POM121L12 | TMEM200A | CD274 |
| ARFGEF1 | DCAF12L1 | FOXG1 | ITGA10 | MYT1L | PREX1 | TNFRSF21 | CDK4 |

TABLE 1-continued

Composition of the biomarker panel

| ASTN1 | DCAF12L2 | FRYL | ITSN1 | NAV3 | PTPLA | TNN | CDKN2A |
|---|---|---|---|---|---|---|---|
| ASTN2 | DCAF4L2 | GBA3 | KCNA5 | NEUROD4 | RALYL | TNR | ESR1 |
| AVPR1A | DCLK1 | GBP7 | KCNB2 | NFE2L2 | RFX5 | TRHDE | FBXW7 |
| BCHE | DCSTAMP | GJA8 | KCNC2 | NLGN4X | RIN3 | TRIM58 | KEAP1 |
| BPIFB4 | DDI1 | GPR139 | KCNJ3 | NLRP3 | RNASE3 | TRPS1 | MLH1 |
| C6 | DLGAP2 | GRIA2 | KCTD8 | NMUR1 | ROBO2 | UGT3A2 | MSH2 |
| C6orf118 | DMD | GRIK3 | KEAP1 | NOL4 | SEMA5B | USH2A | MSH6 |
| CA10 | DNTTIP1 | GRIN2B | KIAA1211 | NPAP1 | SLC18A3 | USP29 | NF2 |
| CACNA1E | DOCK3 | GRIN3B | KIF17 | NR0B1 | SLC39A12 | VPS13B | PDCD1LG2 |
| CDH12 | DSC3 | GRM1 | KIF19 | NRXN1 | SLC6A5 | WBSCR17 | PMS2 |
| CDH18 | DSCAM | GRM5 | KLHL3 | NXPH4 | SLC8A1 | WIPF1 | PTEN |
| CDH8 | EGFLAM | GRM8 | KPRP | NYAP2 | SLITRK1 | WSCD2 | RB1 |
| CDH9 | EPHA5 | GSX1 | LPPR4 | OPRD1 | SLITRK4 | ZC3H12A | SMAD4 |
| CDKN2A | EPHA6 | HCN1 | LRFN5 | P2RY10 | SLITRK5 | ZFPM2 | SMO |
| CHRM2 | EYS | HCRTR2 | LRP1B | PAX6 | SLPI | ZIC1 | STK11 |
| CNTN5 | FAM135B | HEBP1 | LRRC7 | PCDH15 | SMAD4 | ZIC4 | VHL |
| CNTNAP2 | FAM151A | HECW1 | LRRTM1 | PDYN | SOX9 | ZNF521 | APC |
| CPXCR1 | FAM5B | HS3ST4 | LRRTM4 | PDZRN3 | SPTA1 | ZSCAN1 | BRCA1 |
| CPZ | FAM5C | HS3ST5 | LTBP4 | PGK2 | ST6GALNAC3 | N/KRAS | BRCA2 |
| CRMP1 | FAM71B | HTR1A | MAP2 | PHACTR1 | STK11 | MET | EGFR |
| ALK | PDGFRA | RAF1 | JAK3 | NFE2L2 | TSC2 | MTOR | PIK3R1 |
| BRAF | RET | RNF43 | KDR | NTRK1 | TSC1 | MAP2K2 | PIK3CA |
| DPYD | ROS1 | TERT promoter | MAP2K1 | PDGFRB | KIT | UGT1A1 | PTCH1 |

In some embodiments, the invention further includes a step of improving the biomarker panel based on the results obtained from the clinical samples. In some embodiments, the invention includes the steps of analyzing the correlation between the presence of a biomarker in the cell-free DNA from a statistically significant number of patients and A) RFS, B) TTR (or DFS), and C) OS (See FIGS. 2 and 3). The biomarkers showing a predictive correlation are to be included in the panel. The biomarkers not showing a statistically significant predictive correlation are to be excluded from the panel.

The invention includes a step of identifying the patient as likely or not likely to experience recurrence of the cancer. The identification is based on whether the mutations in the biomarkers of the panel were found during the sequencing step. In some embodiments, several mutations, e.g., mutations in 1, 2, 3, 4 or more biomarkers are found while no mutations in other biomarkers are found. The patient is identified as likely to experience recurrence if any mutations are found.

In some embodiments, the invention includes a step of statistical analysis to determine a clinically relevant prediction for a patient. In some embodiments, the prediction is selected from Recurrence Free Survival (RFS), Total Time to Recurrence (TTR) and Overall Survival (OS).

In some embodiments, the method includes an analysis algorithm for scoring the mutations identified during the sequencing step. The algorithm may contain steps of mutation detection, mutation frequency scoring, error correction (including deduplication, using barcodes to eliminate errors) and final determination whether the sample is mutation-positive. In some embodiments, the sample is scored as mutation-positive for a particular biomarker from the panel when the frequency of a mutated allele (variant allele frequency, VAF) exceeds a certain threshold. In some embodiments, the threshold is 5% but other thresholds may be used based on the condition of the sample. For example, a tumor sample with low tumor content may have a lower threshold (e.g., <5% of mutant allele frequency, VAF) for the sample to be scored as mutation-positive. In some embodiments, the algorithm also accounts for the germ-line variations in the biomarkers. For example, a biomarker known to have high level of variation in the germline (>1% ExAC, FIG. 1) may not be scored as mutant In some embodiments, the method further comprises a step of administering additional therapy or modifying a therapy regimen based on the finding of mutations. In some embodiments, if the patient is identified as likely to experience recurrence, the existing or initial regiment of chemotherapy is increased. E.g., in some embodiments, oxaliplatin or FOLFOX are administered or their doses are increased. In some embodiments, adjuvant therapy is added to the existing or proposed chemotherapy or to a reduced regimen of chemotherapy. In some embodiments, the regimen of FOLFOX is reduced but adjuvant therapy is added such as immune modulating agents, molecular targeted agents or additional chemotherapeutic agents.

The examples set forth below show that patients having ctDNA in their blood after surgery had a statistically significant higher risk of recurrence as compared to patients with no ctDNA post-surgery. Different analytical methods may be used, i.e., different groups of biomarkers can be analyzed to assess the patient's prognosis. A comparison of three exemplary methods is shown in Table 2.

TABLE 2

Comparison between the method of Tie et al. and the present invention (analytical methods 1, 2 and 3)

| Recurrence Free Survival | Clinical Performance for RFS (n = 33) | | | |
|---|---|---|---|---|
| | Sn. | Sp. | PPV | NPV |
| A1: Tie et al Genes, Hot Exons, Maximal AF Variant | 15.2% | 100% | 100% | 78.3% |
| A2: Tie et al Genes, All Exons, All Variants | 24.2% | 100% | 100% | 80.9% |
| A3: Present invention | 33.3% | 100% | 100% | 83.5% |

| Relapse Detection | Clinical Performance for RD (n = 20) | | | |
|---|---|---|---|---|
| | Sn. | Sp. | PPV | NPV |
| A1: Tie et al Genes, Hot Exons, Maximal AF Variant | 25.0% | 100% | 100% | 88.4% |
| A2: Tie et al Genes, All Exons, All Variants | 40.0% | 100% | 100% | 90.8% |
| A3: Present invention | 50.0% | 99% | 91% | 92.5% |

| Overall Survival | Clinical Performance for OS (n = 15) | | | |
|---|---|---|---|---|
| | Sn. | Sp. | PPV | NPV |
| A1: Tie et al Genes, Hot Exons, Maximal AF Variant | 13.3% | 97% | 40% | 89.9% |
| A2: Tie et al Genes, All Exons, All Variants | 13.3% | 95% | 25% | 90.1% |
| A3: Present invention | 20.0% | 94% | 27% | 91.0% |

Figure 2:
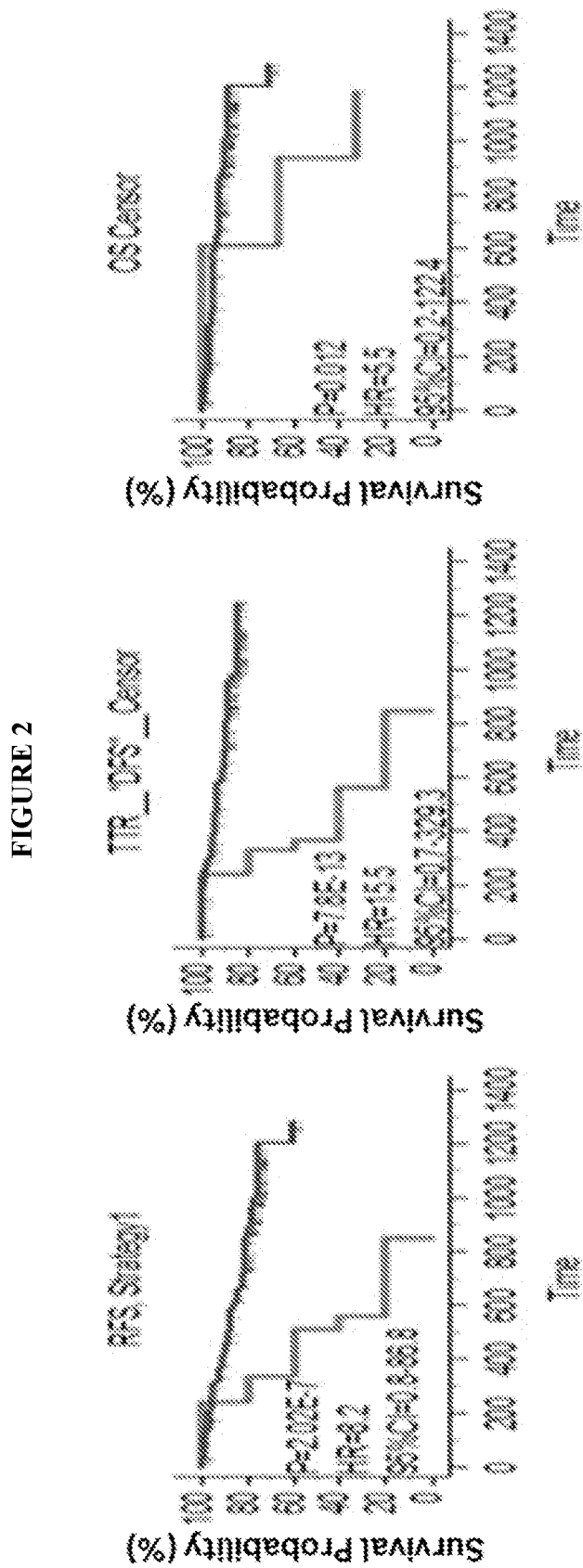
FIG. 2 illustrates Kaplan Meier graphs that determine patient prognosis based on detection of ctDNA.
Figure 3:
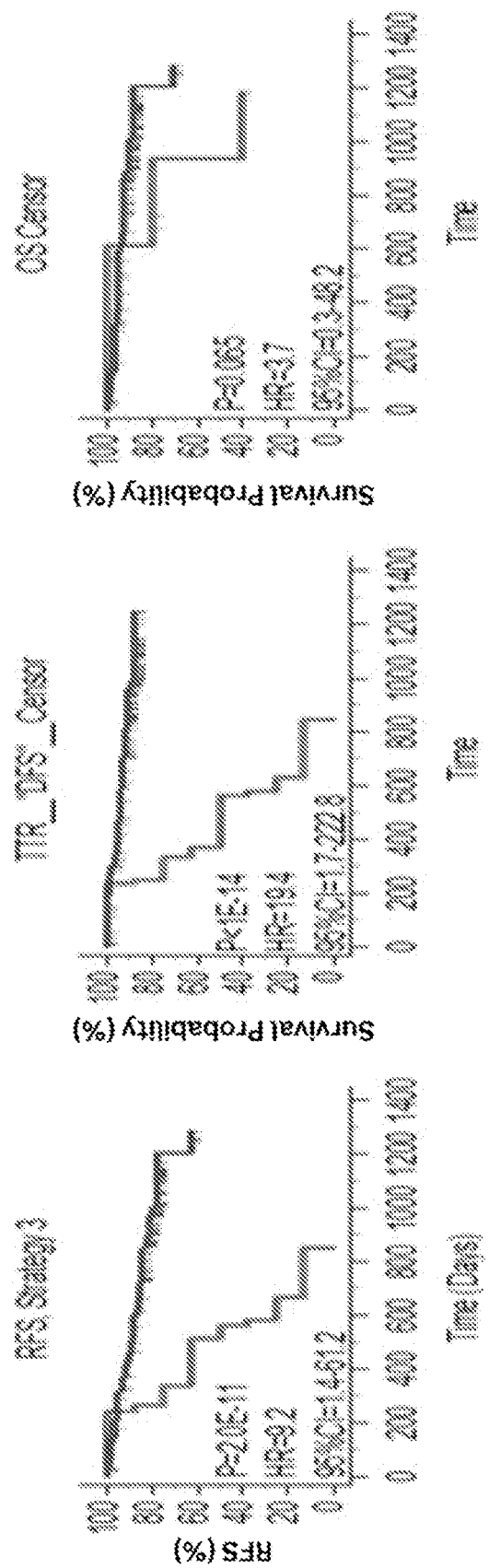
FIG. 3 illustrates Kaplan Meier graphs that determine total time to recurrence (TTR) based on stage of disease and detection of ctDNA.
Figure 4:
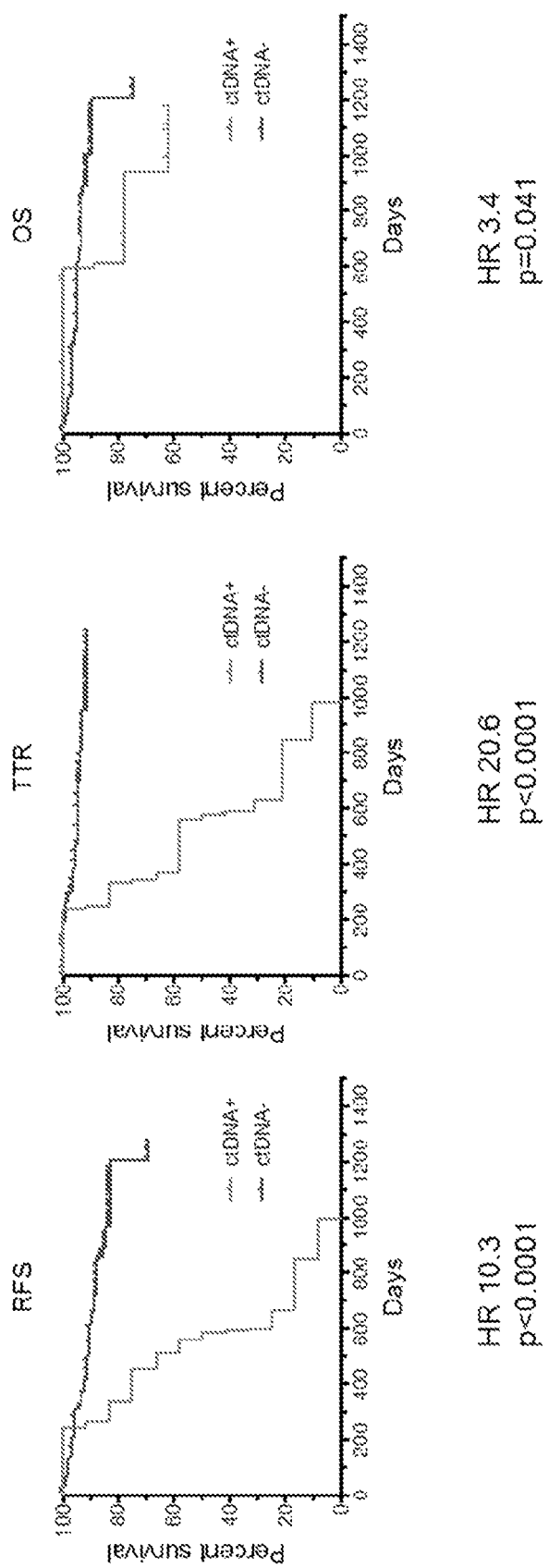
FIG. 4 illustrates Kaplan Meier graphs for analysis method 1 to determine patient prognosis.
Figure 5:
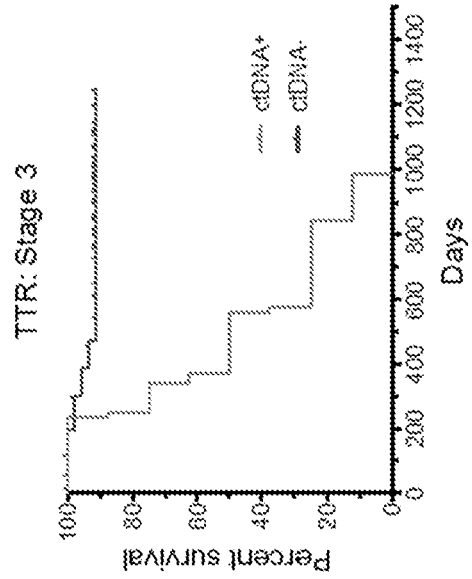
FIG. 5 illustrates Kaplan Meier graphs for analysis method 2 to determine patient prognosis.
Figure 5:
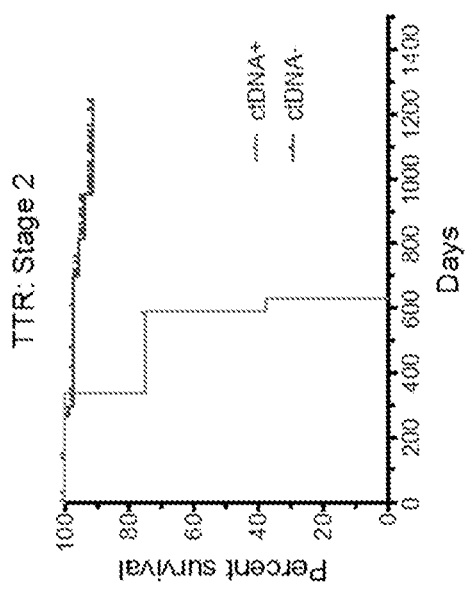

Sn—sensitivity
Sp—specificity
PPV—positive predictive value
NPV—negative predictive value For example, analytical method 1 (A1) (FIG. 1) evaluated only genes from the AVENIO® ctDNA Analysis Kits that overlapped with the mutated genes identified by Tie et al. For each tissue sample tested, only the mutation that was identified at the highest mutation allele frequency was used for monitoring of post-surgical mutation status. Results in FIG. 2 show the difference in relapse-free survival (RFS), time to recurrence/disease free survival (TTR, DFS) and overall survival (OS) for samples that were ctDNA was or was not detected using analytical method 1. Survival predictions for analytical methods 2 (A2) and 3 (A3) are shown in FIGS. 3 and 4. For analytical method 2, all mutations that were identified in each tissue sample using the 10 genes that overlapped between Tie et al. and the AVENIO® ctDNA Analysis Kits were used to monitor patients for the presence of ctDNA after surgical intervention. In analytical method 3, all mutations identified in tissue using the AVENIO® ctDNA Analysis Kits were used to detect the presence or absence of ctDNA in post-surgical plasma samples. All survival outcomes were significantly different except for OS with analytical method 2. For Stage II and Stage III patients, TTR for samples that were ctDNA was or was not detected was significantly different in each stage separately.

The data using analysis method 3 shows that as a measure of relapse-free survival, including disease related recurrence and any death, patients with ctDNA had a 10-fold increased risk of disease recurrence. As a measure of time to recurrence, that excludes death as an event, patients with ctDNA had a 20-fold increased risk of disease recurrence. Overall survival was lower for patients with ctDNA present in blood. Subanalyses revealed that the higher risk of recurrence in case of mutational detection in plasma is statistically significant in stage II and stage III colorectal cancer patients. This supports the prognostic value of the assay to predict recurrence of disease.

The method disclosed herein is an improvement over the prior art method of predicting recurrence of colorectal cancer described in Tie et al. The predictive value of the method of the invention has been improved by including both stage II and stage III patients. The predictive value of the method has been further improved by using samples only from patients with clear histological margins of the tumor (R0 patients) and excluding patients with microscopic residual disease in surgically resected tissue (R1 patients). The improved method has a greater sensitivity for low disease burden patients as compared to Tie et al. as is seen in Table 2. The method of the present invention can reliably detect one copy of mutant DNA in 4 ml of plasma.

The methodology described will be the basis for decision making on the use of adjuvant chemotherapy in stage II. Further it will be used for decision making in stage III patients to a) reduce the oxaliplatin if selecting adjuvant chemotherapy or b) add additional adjuvant therapy beyond FOLFOX such as immune modulating agents, molecular targeted agents or additional chemotherapeutic agents. Two additional analytic options are provided to identify the same recurrence risks as analysis methods 1-3. The AVENIO ctDNA Analysis Kits can also detect cancer mutations in stage 1 disease.

EXAMPLES

Example 1. Detecting Tumor DNA in Colorectal Cancer (CRC) Patients Following Surgery In this example, the next-generation sequencing based AVENIO® ctDNA Surveillance Kit (Roche Sequencing Solutions, Pleasanton, Cal.) was used to identify single nucleotide variants (SNVs) in tumor tissue within a cohort of 145 Stage II and III CRC pts following R0 surgical resection (n=86 and 59 respectively; median follow-up=32.1 mo). The samples were collected 1-21 days post-surgery (mean—10 days). The same assay was used to monitor ctDNA with a single post-operative blood sample (mean surgery-to-phlebotomy time: 10 days). Regions from 197 genes recurrently mutated in CRC were interrogated, and pts were classified as ctDNA positive (+) or negative (−) in plasma based on the detection of SNVs previously identified in tumor tissue. The experimental workflow is shown in FIG. 1.

Results are shown in FIGS. 2-5. Variants were identified in 99% of tumors (n=144) with a median of 4 SNVs/sample (range 1-24) and all post-operative plasma samples were successfully profiled. Pts with detectable ctDNA (n=12) displayed a significantly shorter 2-year relapse-free survival (RFS; 17% vs 88%; HR 10.3; 95% CI 2.3-46.9; p<0.00001), time to recurrence (TTR; HR 20.6; 95% CI 3.1-139.0; p<0.00001) and overall survival (OS; HR 3.4; 95% CI 0.5-25.8; p=0.041) than ctDNA-pts (n=132). 11 (92%) of ctDNA+ pts developed recurrence compared to 9 (7%) of ctDNA− pts. Monitoring multiple variants doubled sensitivity of MRD detection compared to tracking a single driver mutation. TTR was shorter in ctDNA+vs ctDNA− Stage II (HR 23.1, 95% CI 0.28-1900.4; p<0.00001) and stage III pts (HR 17.9; 95% CI 2.7-117.3, p<0.00001). TTR of Stage II and III ctDNA− pts was similar (p=0.7).

A further analysis of this study was performed using a variation to the method shown in FIG. 1. In this analysis, 145 CRC tumors and paired POST plasma samples were analyzed using adaptive variant calling without paired germline on tumors and post-treatment plasma. The filters used for classification as a true somatic variant were 1) 7% tumor variant allele frequency; 2)<1% frequency in the ExAC database; 3) Nonsynonymous only; 4)<20% post-treatment variant allele frequency; 5) Exclude CACNA1E variants. Using this analysis, variants were still identified in the same patients (n=144). However, there were now a median of 5 SNVs/sample (range 1-28). The same 12 ctDNA+ patients were identified, hence the results for TTR, RFS and OS were unchanged.

The invention claimed is:

1. A method of treating a patient having a colorectal tumor following surgery, wherein the method consists of the following steps:
   (a) obtaining a cell-free DNA (cfDNA) sample from a blood sample obtained from the patient following surgery;
   (b) sequencing each of the following genes to detect the presence of one or more mutations in the following genes: ABCC5, CSMD1, FAT1, HTR1E, MAP7D3, PIK3CA, SV2A, AR, ABCG2, CSMD3, FBN2, HTR2C, MKRN3, PIK3CG, T, CCND1, ACTN2, CTNNB1, FBXL7, IFI16, MMP16, PKHD1L1, THSD7A, CCND2, ADAMTS12, CTNND2, FBXW7, IL7R, MTX1, POLE, TIAM1, CCND3, ADAMTS16, CYBB, FCRL5, INSL3, MYH7, POM12IL12, TMEM200A, CD274, ARFGEF1, DCAF12L1, FOXG1, ITGA10, MYT1L, PREX1, TNFRSF21, CDK4, ASTN1, DCAF12L2, FRYL, ITSN1, NAV3, PTPLA, TNN, CDKN2A, ASTN2, DCAF4L2, GBA3, KCNA5, NEUROD4, RALYL, TNR, ESR1, AVPR1A, DCLK1, GBP7, KCNB2, NFE2L2, RFX5, TRHDE, FBXW7, BCHE, DCSTAMP, GJA8, KCNC2, NLGN4X, RIN3, TRIM58, KEAP1, BPIFB4, DDI1, GPR139, KCNJ3, NLRP3, RNASE3, TRPS1, MLH1, C6, DLGAP2, GRIA2, KCTD8, NMUR1, ROBO2, UGT3A2, MSH2, C6orf118, DMD, GRIK3, KEAP1, NOL4, SEMA5B, USH2A, MSH6, CA10, DNTTIP1, GRIN2B, KIAA1211, NPAP1, SLC18A3, USP29, NF2, CACNA1E, DOCK3, GRIN3B, KIF17, NR0B1, SLC39A12, VPS13B, PDCDILG2, CDH12, DSC3, GRM1, KIF19, NRXN1, SLC6A5, WBSCR17, PMS2, CDH18, DSCAM, GRM5, KLHL31, NXPH4, SLC8A1, WIPF1, PTEN, CDH8, EGFLAM, GRM8, KPRP, NYAP2, SLITRK1, WSCD2, RB1, CDH9, EPHA5, GSX1, LPPR4, OPRD1, SLITRK4, ZC3H12A, SMAD4, CDKN2A, EPHA6, HCN1, LRFN5, P2RY10, SLITRK5, ZFPM2, SMO, CHRM2, EYS, HCRTR2, LRP1B, PAX6, SLPI, ZIC1, STK11, CNTN5, FAM135B, HEBP1, LRRC7, PCDH15, SMAD4, ZIC4, VHL, CNTNAP2, FAM151A, HECW1, LRRTM1, PDYN, SOX9, ZNF521, APC, CPXCR1, FAM5B, HS3ST4, LRRTM4, PDZRN3, SPTA1, ZSCAN1, BRCA1, CPZ, FAM5C, HS3ST5, LTBP4, PGK2, ST6GALNAC3, N/KRAS, BRCA2, CRMP1, FAM71B, HTR1A, MAP2, PHACTR1, STK11, MET, EGFR, ALK, PDGFRA, RAF1, JAK3, NFE2L2, TSC2, MTOR, PIK3R1, BRAF, RET, RNF43, KDR, NTRK1, TSC1, MAP2K2, PIK3CA, DPYD, ROS1, TERT promoter, MAP2K1, PDGFRB, KIT, UGT1A1, and PTCH1; and
   (c) administering adjuvant chemotherapy if the presence of one or more mutations is detected in step (b).

2. The method of claim 1, wherein the patient is a stage II colorectal cancer patient.

3. The method of claim 1, wherein the patient is a stage III colorectal cancer patient.

4. The method of claim 1, wherein the adjuvant chemotherapy therapy is a therapy selected from: immune modulating agents, molecular targeted agents, and additional chemotherapeutic agents.

* * * * *